(12) United States Patent
Cole et al.

(10) Patent No.: US 7,048,384 B2
(45) Date of Patent: May 23, 2006

(54) MULTIPLE SCENE PROJECTION SYSTEM

(75) Inventors: Barrett E. Cole, Bloomington, MN (US); Robert E. Higashi, Shorewood, MN (US)

(73) Assignee: Honeywell International Inc., Morristown, NJ (US)

( * ) Notice: Subject to any disclaimer, the term of this patent is extended or adjusted under 35 U.S.C. 154(b) by 194 days.

(21) Appl. No.: 10/351,154

(22) Filed: Jan. 24, 2003

(65) Prior Publication Data

US 2004/0227906 A1 Nov. 18, 2004

(51) Int. Cl.
| | |
|---|---|
| G03B 21/26 | (2006.01) |
| G03B 21/00 | (2006.01) |
| G03B 21/14 | (2006.01) |
| G02B 21/00 | (2006.01) |
| G02F 1/1335 | (2006.01) |
| G01J 1/00 | (2006.01) |
| H04N 9/64 | (2006.01) |

(52) U.S. Cl. ............... 353/94; 353/31; 353/48; 353/84; 353/121; 359/583; 359/629; 359/639; 349/108; 250/495.1; 250/504 R; 348/33; 348/47; 348/38

(58) Field of Classification Search ........... 353/94, 353/30–31, 48, 84, 121, 10; 359/583, 479, 359/629, 639; 345/15; 349/108; 250/495.1, 250/504 R; 102/213; 348/33, 47, 38

See application file for complete search history.

(56) References Cited

U.S. PATENT DOCUMENTS

| | | | | | |
|---|---|---|---|---|---|
| 3,580,978 | A | * | 5/1971 | Ebeling | 434/43 |
| 3,744,423 | A | | 7/1973 | Ertsgaard | 102/213 |
| 4,190,856 | A | * | 2/1980 | Ricks | 348/42 |
| 5,306,913 | A | | 4/1994 | Noack et al. | 250/338.5 |
| 5,319,214 | A | | 6/1994 | Gregory et al. | 250/504 R |
| 5,568,186 | A | | 10/1996 | Althouse | 348/33 |
| 5,600,148 | A | | 2/1997 | Cole et al. | 250/495.1 |
| 5,883,681 | A | * | 3/1999 | Kono et al. | 348/751 |
| 5,949,081 | A | * | 9/1999 | Ashley et al. | 250/493.1 |
| 5,956,180 | A | * | 9/1999 | Bass et al. | 359/479 |
| 5,973,383 | A | | 10/1999 | Cole et al. | 257/536 |
| RE37,146 | E | | 4/2001 | Cole et al. | 250/495.1 |
| 6,210,494 | B1 | | 4/2001 | Cole et al. | 148/237 |
| 6,297,511 | B1 | | 10/2001 | Syllaios et al. | 250/495.1 |
| 6,316,777 | B1 | | 11/2001 | Parrish et al. | 250/495.1 |
| 6,751,005 | B1 | * | 6/2004 | Barnick et al. | 359/290 |
| 6,778,257 | B1 | * | 8/2004 | Bleeker et al. | 355/67 |
| 6,906,762 | B1 | * | 6/2005 | Witehira et al. | 349/73 |

\* cited by examiner

*Primary Examiner*—William B Perkey
*Assistant Examiner*—Magda Cruz
(74) *Attorney, Agent, or Firm*—Kris T. Fredrick

(57) ABSTRACT

A projection system for presenting infrared scenes having biological and chemical agents, simulants and objects such as battlefield items. The generated scenes are primarily for the evaluation of infrared sensors, cameras and stand-off detectors. The system may have two or more projectors that combine various scenes into one scene having components with modified or imposed spectra signatures. Also, the system may generate a dynamic series of scenes that show synthetic scenarios of moving objects, agent clouds, non-toxic simulants and other items.

20 Claims, 12 Drawing Sheets

MULTIPLE SCENE PROJECTION SYSTEM

BACKGROUND

The invention pertains to infrared projectors and particularly to infrared projectors for generating a scene with various simulated objects in it for detection.

Some infrared projectors are designed to test infrared detectors. Such projectors provide various scenes to determine the sensitivity, speed and bandwidth of the infrared detectors.

SUMMARY OF THE INVENTION

The invention is an infrared projector or a combination of infrared projectors that may generate a synthetic scene having toxic chemical and/or biological agents, non-toxic agents or simulants. Agents may be a gas or liquid. "Fluid" is a generic term that includes liquids and gases as species. For instance, air, $CO_2$, water and oil are fluids. The synthetic scene may be utilized for the test and evaluation of infrared chemical and biological detectors, among other things.

DESCRIPTION

Figure 1:
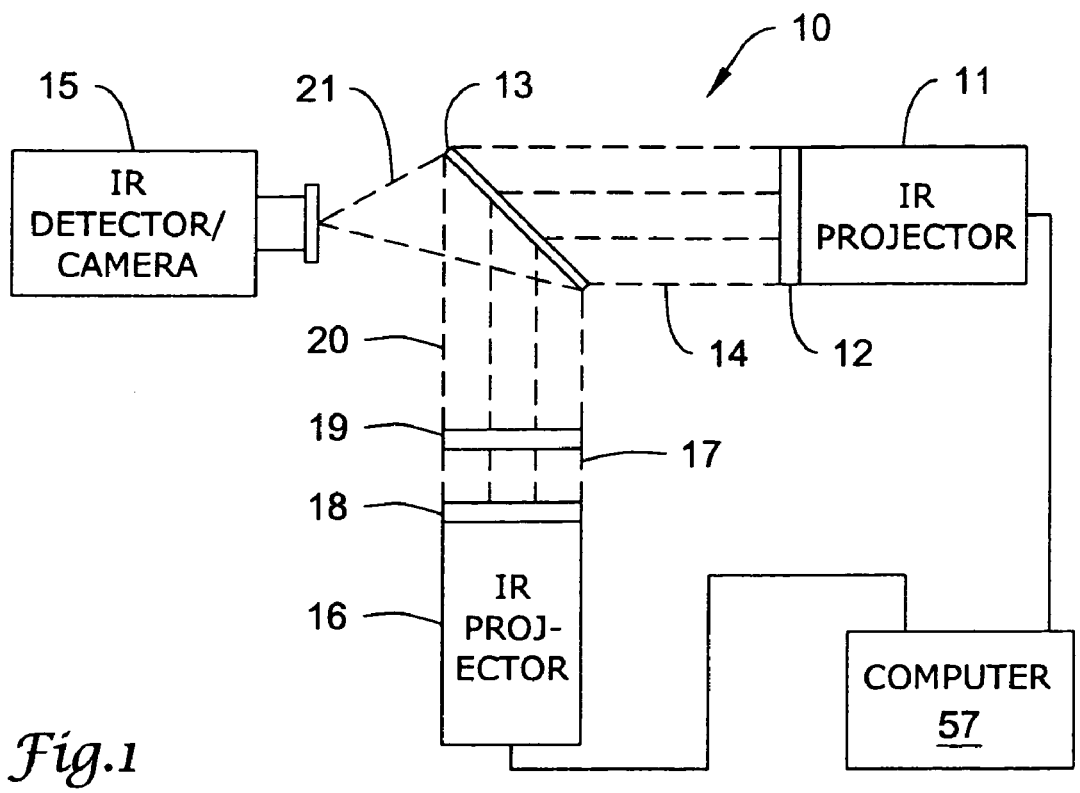
FIG. 1 reveals a two scene infrared projection system.

FIG. 1 shows a multiple scene projection system 10. Projector 11 may project an infrared radiation, light or scene 14 from an array 12 through a beam splitter or combiner 13 onto an infrared detector or camera 15. Projectors 11 and 16 may present scenes via arrays 12 and 18, respectively, which may be generated and coordinated by a computer 57. A computer, though not necessarily shown, may present scenes or portions of them for various projector system configurations described below. Array 12 may provide a normal infrared signature. A projector 16 may project an infrared radiation, light or scene 17 from an array 18. Radiation, light or scene 17 may go through a device, filter, cell or absorber 19 to beam splitter or combiner 13. The terms "filter", "cell" and "absorber" may be used interchangeably. The term "device" may be used in a context which may implicitly or explicitly identify that term. Radiation, light or scene 17 may go into device 19 and comes out as radiation, light or scene 20 which is combined with radiation, light or scene 14 by splitter or combiner 13 into radiation, light or scene 21 (henceforth referred to as a scene). Scene 21 is projected towards camera 15 as if it is from infinity. It's not like a projector's focusing the scene to be displayed on a screen. Scene 21 is essentially a virtual image.

Device 19 may have a toxic or non-toxic biological or chemical agent, simulant or a combination of fluids or substances. Device 19 may be an absorption cell through which scene 17 goes. A battle scene may be simulated with a gas in it having certain spectral characteristics. The test is to determine how well an infrared detector, such as camera 15, can detect the gas and/or simulant of the cell in the projected scene. Additional absorption cells of various gases and/or simulants or mixtures of such gases and simulants may be inserted between array 12 and combiner 13, and between array 18 and combiner 13.

Figure 2:
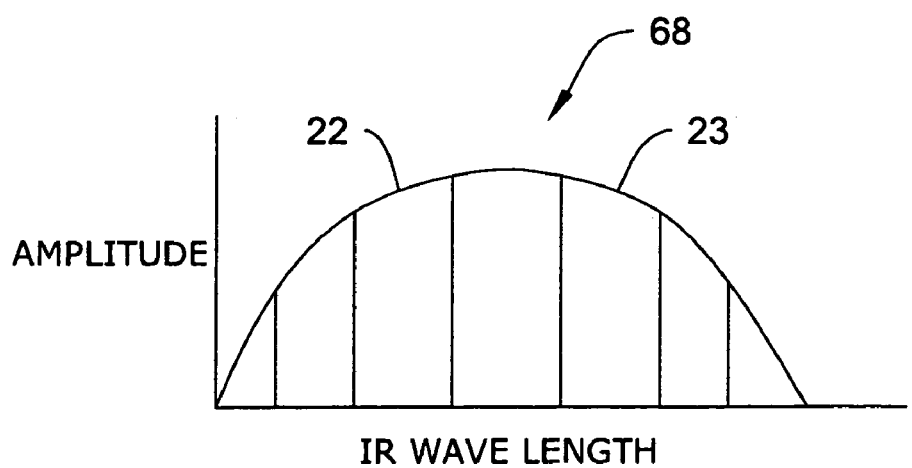
FIG. 2 is a graph of amplitude versus wavelength of a black body radiator.

FIG. 2 is a graph of amplitude versus wavelength representing spectra 68 of a black body radiator. Projectors 11 and 16 may project scenes of the same bandwidth or different bandwidths. Or the projectors may be black body emitters having the spectrum shown in FIG. 2. If projectors 11 and 16 have different bandwidths, one may emit medium wavelength infrared radiation (MWIR) 22 and the other may emit long wavelength infrared radiation (LWIR) 23, as an illustrative example.

Figure 3:
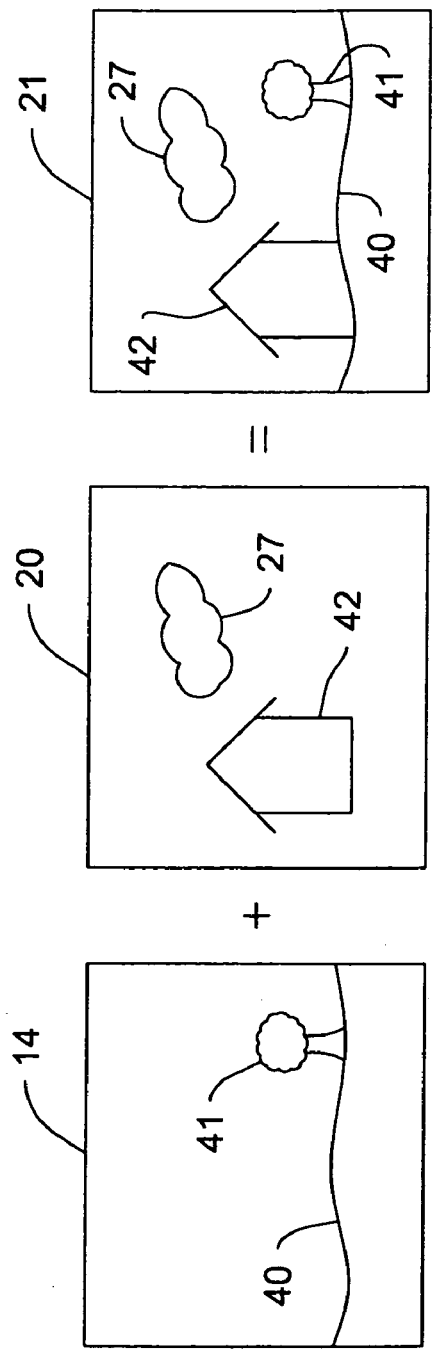
FIG. 3 shows two scenes that are combined into one scene.

FIG. 3 shows a scene 14 having a landscape 40 and a tree 41, and a scene 20 having a building 42 and a cloud 27. Scene 14 may be provided by projector 11 and scene 20 may be provided by projector 16. Scene 20 may be projected through absorption cell 19 and the spectra of the gas in cell 19 may be superimposed on cloud 27 of scene 20. Then scenes 14 and 20 may be put together by combiner 13 into a scene 21. If the bandwidths of scenes 14 and 20 from projectors are the same then combiner 13 may be a "silvered" transparent medium that reflects about one-half of the light that impinges it. The remaining light goes through combiner 13. If scenes 14 and 20 are of different bandwidths then combiner 13 may be a dichromic mirror that transmits a substantial portion of scene 14 and reflects a substantial portion of scene 20. Combiner 13 may be some other mechanism, besides a mirror-like device, for combining scenes 14 and 20.

Figure 4A:
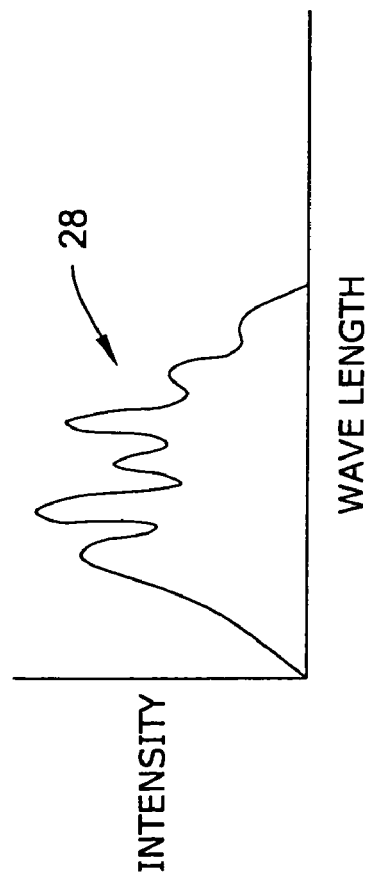
FIG. 4a shows illustrative gas spectra.
Figure 4B:
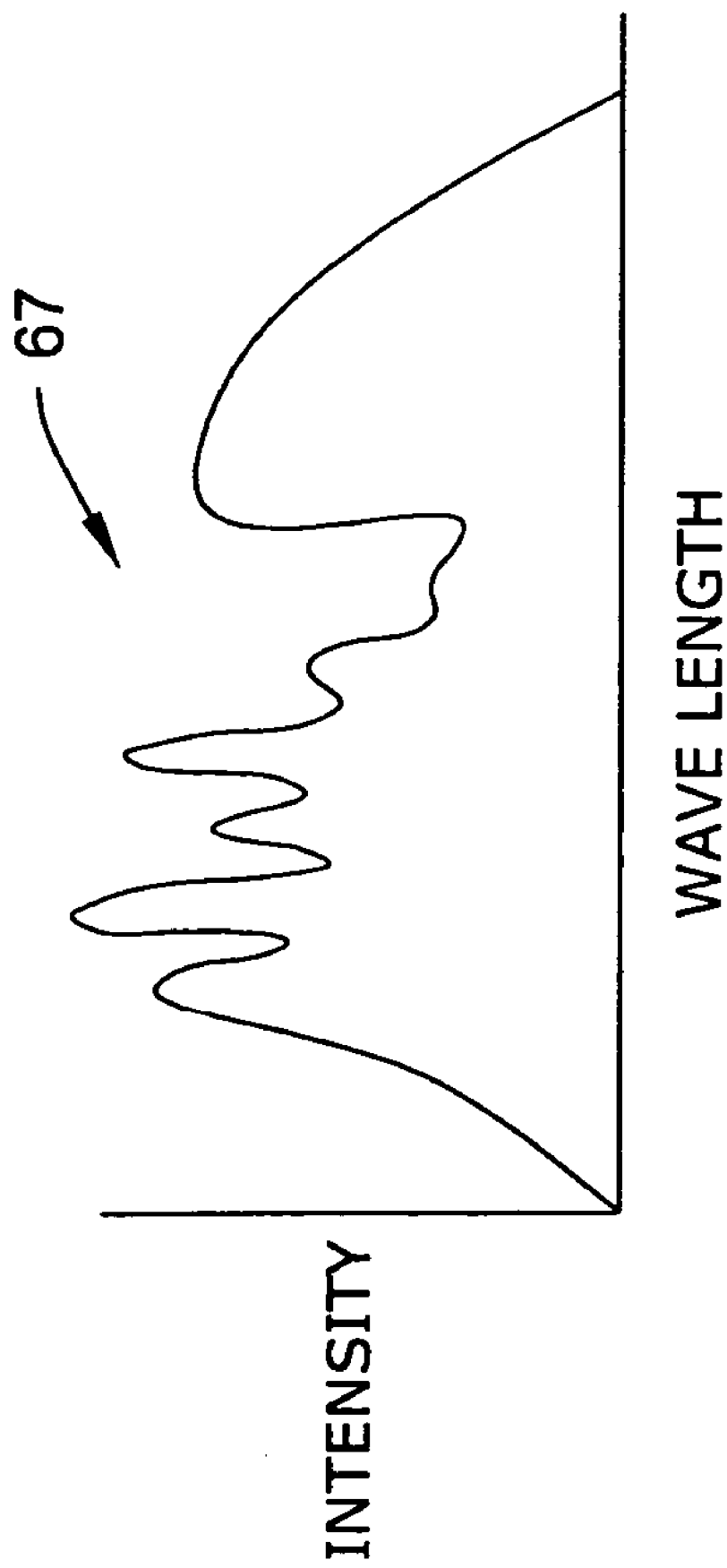
FIG. 4b shows combined black body and gas spectra.

Cloud 27 representing the gas may all originate in one projector or a part of cloud 27 may originate from another projector. Scenes 14 and 20 may be separated electronically, such as pixel by pixel, and combined optically, pixel by pixel. For increased contrast, the background temperature of the scene such as that in scene 14 may be lowed and cloud 27 temperature of scene 20 may be increased. The cloud representing the agent or gas may have a complex signature of spectra peaks or wavelengths as shown by example spectra 28 in the graph of FIG. 4a. FIG. 4b is a graph of curve 67 combining black body spectra 68 of FIG. 2 and gas spectra 28 of FIG. 4a. One test of infrared detector 15 would to be able to identify the gas in the scene having both black body and gas spectra. Detector 15 may need to be tuned to be spectrally sensitive to a particular gas or agent.

The agent or simulant being detected could be any gas, liquid, or substance. Device 19 may be a container having walls that are transparent. The pressure of the gas in the container may be set at an acceptable value for appropriate absorption. The absorption cross-section of a fluid in a cell may be noted. For example, there may be a mixture of gases in device 19. These gases may have complex spectra that detector 15 may decipher and thus identify the gases and their respective quantities. Each additional array with a gas cell in front of it is filled with the proper agent or simulant (fluid or other substance) at the proper pressure to represent the integrated absorption-path length infrared signal attenuation.

Figure 5:
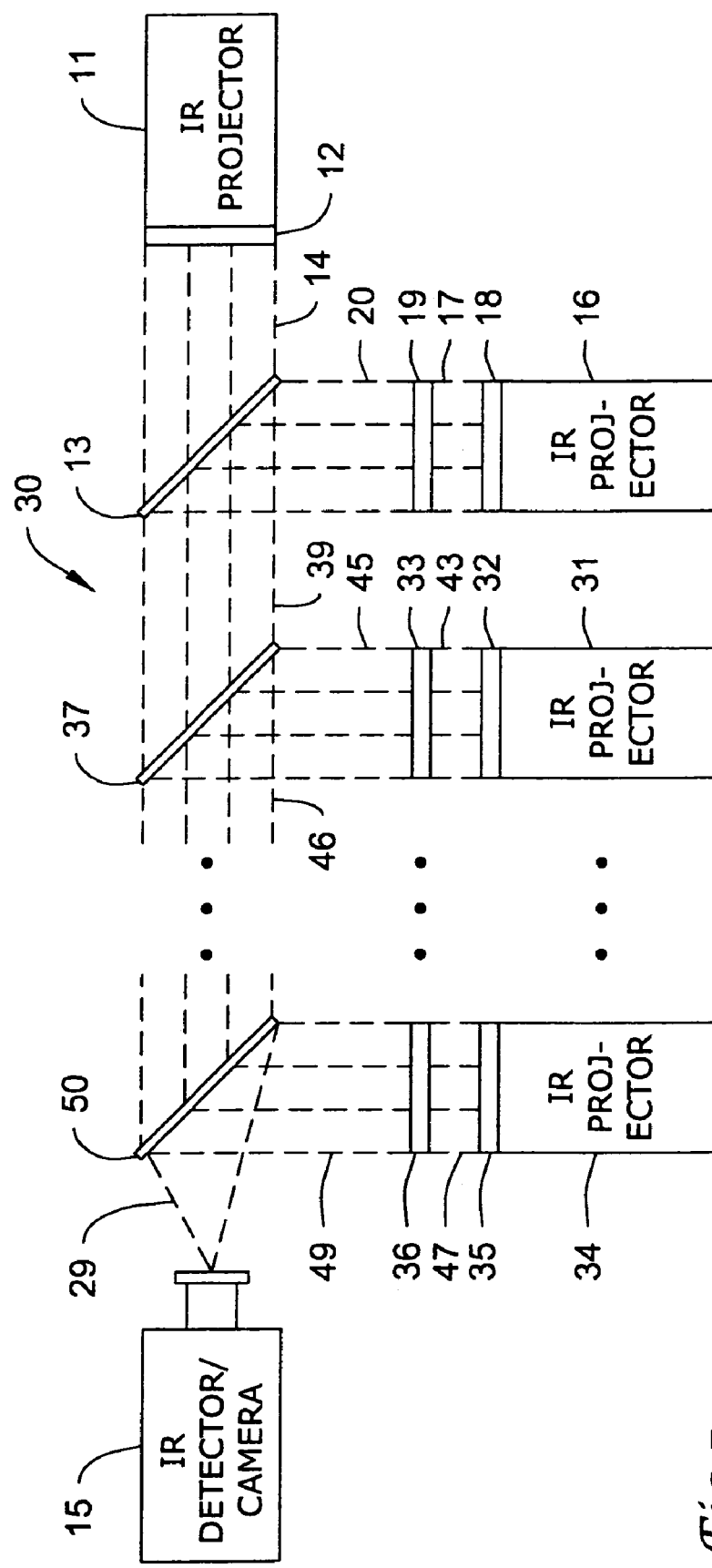
FIG. 5 reveals a multiple scene infrared projection system.

A plurality of gases may be utilized in the scene projector system in another manner. FIG. 5 shows a system 30 having three or more projectors that may be utilized. A third projector 31 with an array 32 could be added with a gas cell 33 for containing a second gas to be added to a scene 29 for camera 15 to detect. If desired, additional projectors may be added. A final projector 34 may be the second, third or N-th projector along with the respective array 35 and cell 36. Projector system 30 may use silvered or the like splitters or combiners, or di- or multi-chromic splitters or combiners. Other forms of combining the scenes, such as light couplers, may be incorporated.

Figure 6:
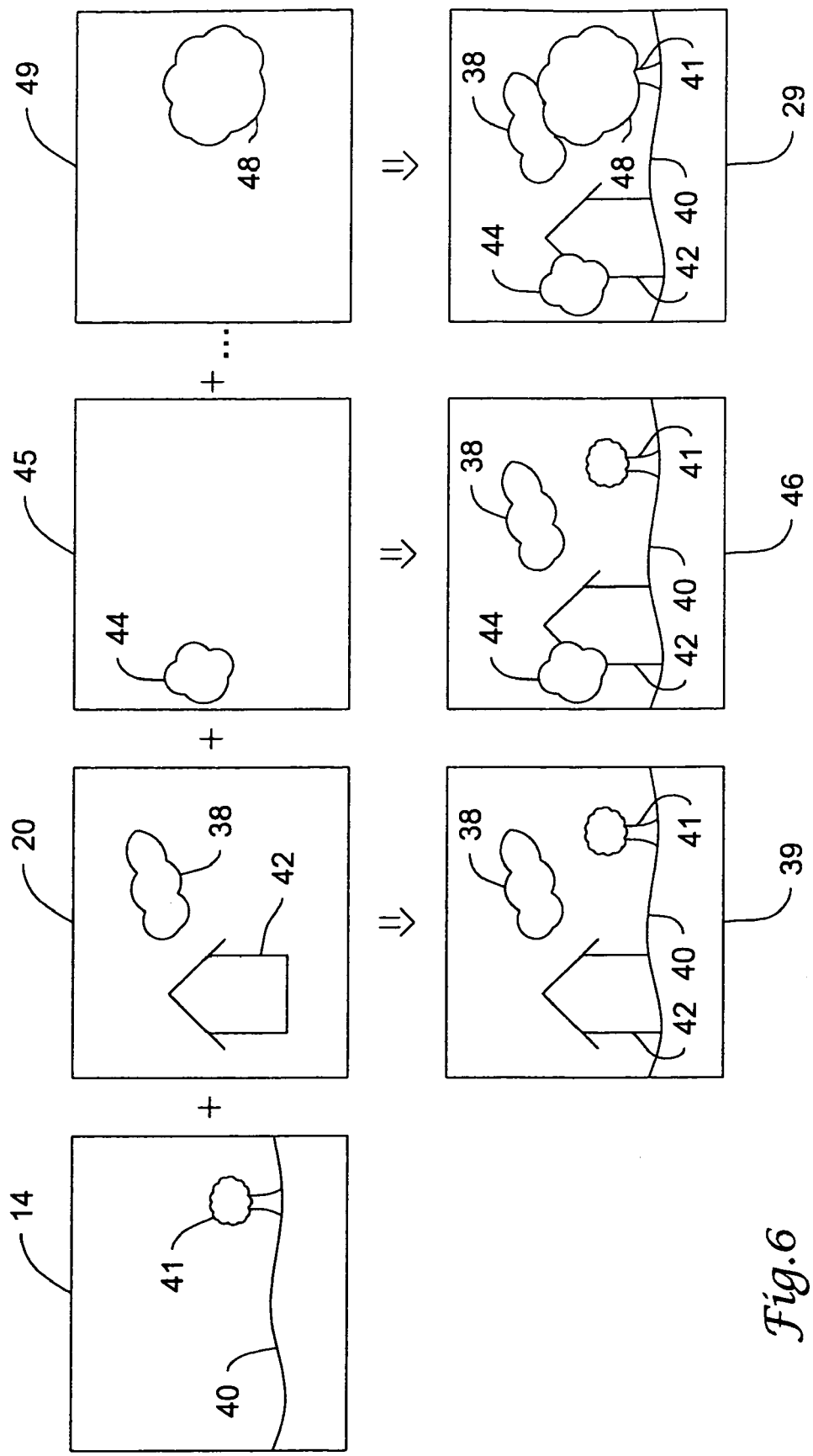
FIG. 6 shows the various scenes associated with the projection system of FIG. 5.

A scene 14 may be emanated by projector 11 via array 12. Scene 14, having a landscape 40 and a tree 41, goes to combiner 13, as shown in FIG. 5. The scenes and their combinations are revealed in FIG. 6. Projector 16 emanates a scene 17 via array 18 through gas cell 19. A building 42 and a cloud 38 make up scene 20 as it emanates from cell 19. Cloud 38 picks up the spectra signature of the gas in cell 19. Scenes 14 and 20 are put together as a scene 39 by combiner 13. Scene 39 goes to combiner 37. Projector 31 emanates a scene 43 via an array 32 through gas cell 33. A cloud 44 makes up scene 45 as it emanates from cell 33. Cloud 44 picks up the spectra signature of the gas in cell 33. Scenes 39 and 45 are put together as a scene 46 by combiner 37. There may be more projectors as needed through N-th projector 34. For this illustrative example, one may assume that only four projectors contribute to the resultant scene 21. N-th projector 34 emanates a scene 47 having a cloud 48 via a cell 36. Cloud 48 picks up the spectra signature of the gas in cell 36 as it emerges from cell 36 as a scene 49. Scenes 46 and 49 are put together as scene 29 by combiner 50. Actually, scene 29 is a combination of scenes 14, 20, 45 and 49. There are at least three gases that camera 15 may detect and identify. Some or all of the gases may be different, the same or mixtures of various fluids. Of course, as indicated above, other fluids and/or objects may be added to resultant scene 29 from more projectors in system 30.

Figure 7:
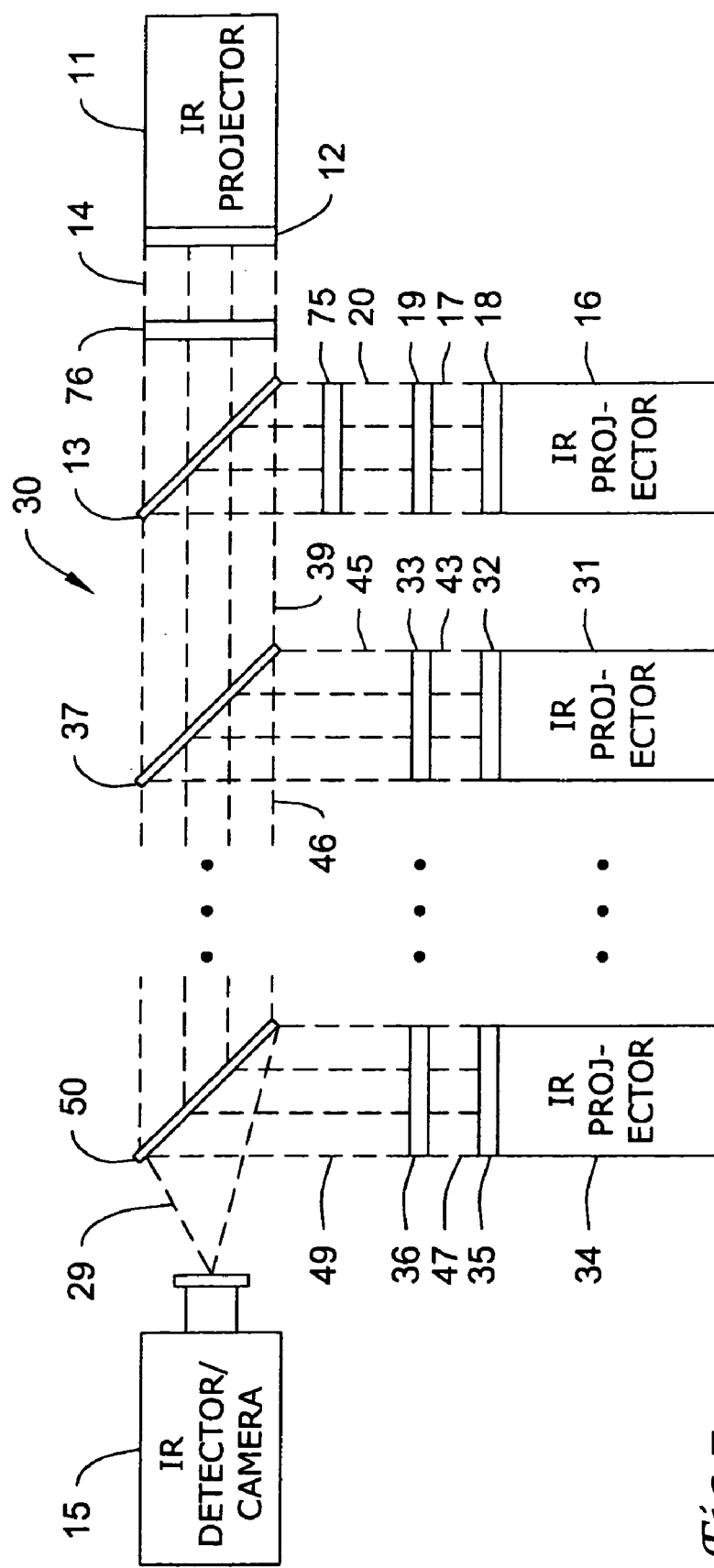
FIG. 7 reveals the system of FIG. 5 with additional filters.
Figure 8A:
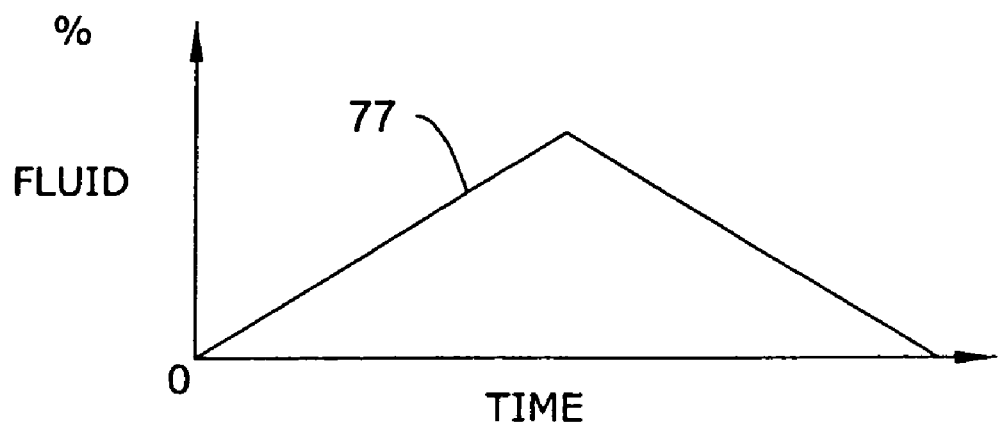
FIGS. 8a and 8b show illustrative examples of dynamics of a fluid composition in a filter.
Figure 8B:
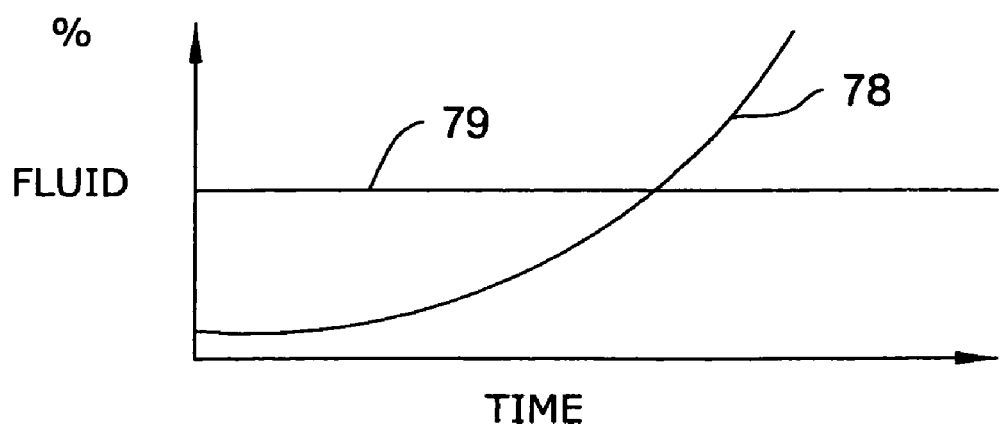

As shown in FIG. 7, projector system 30 may have additional gas cells 75 and 76 in front of projectors 16 and 11, respectively. Scene 14 in FIG. 6 may have a superimposition of spectra of a gas in cell 76. It may be over items 40 and 41. Scene 20 after passing through cell 19 may have other fluid spectra imposed on it. Cell 75 may impose those spectra on scene 20. For instance, cloud 38 may have a mixture of two gases in this IR scene simulation due to cells 19 and 75. The percentage of the two gases relative to the total composition may vary over time. For example, FIG. 8a may show a curve 77 of the percentage of a gas of cell 75 in cloud 38 over time. Another gas of cell 19 may be the remaining percentage of gas in the composition of cloud 38. Cloud 38 may also have a percentage of water vapor. Cell 75 may have a mixture of various gases. The same may be true for cell 19. Curves of FIG. 8b reveal other examples of percentages 78 and 79 over time of gas compositions in a scene displaying objects such as cloud 38. System 30 may have any arrangement of projectors and cells to compose IR scenes of various scenarios.

Figure 9:
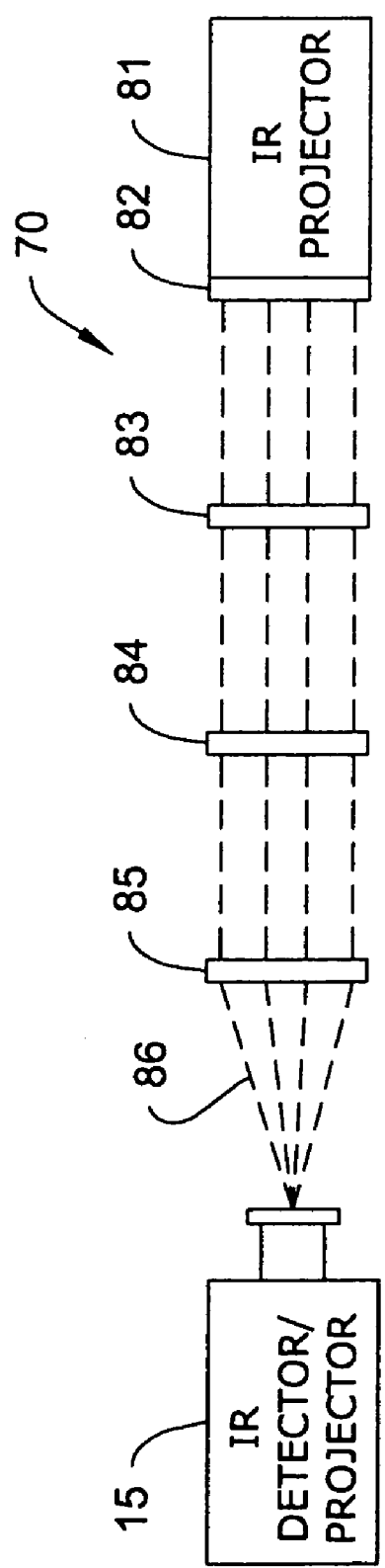
FIG. 9 illustrates a single projector system having multiple filters.

FIG. 9 shows an IR scene projection system 70 with array 82 having one projector 81 and a multitude of cells. In this instance, there are cells 83, 84 and 85 that may have any combination of fluids for a display of desired spectra for items in a projected IR scene 86 for detection by IR camera 15.

Figure 10:
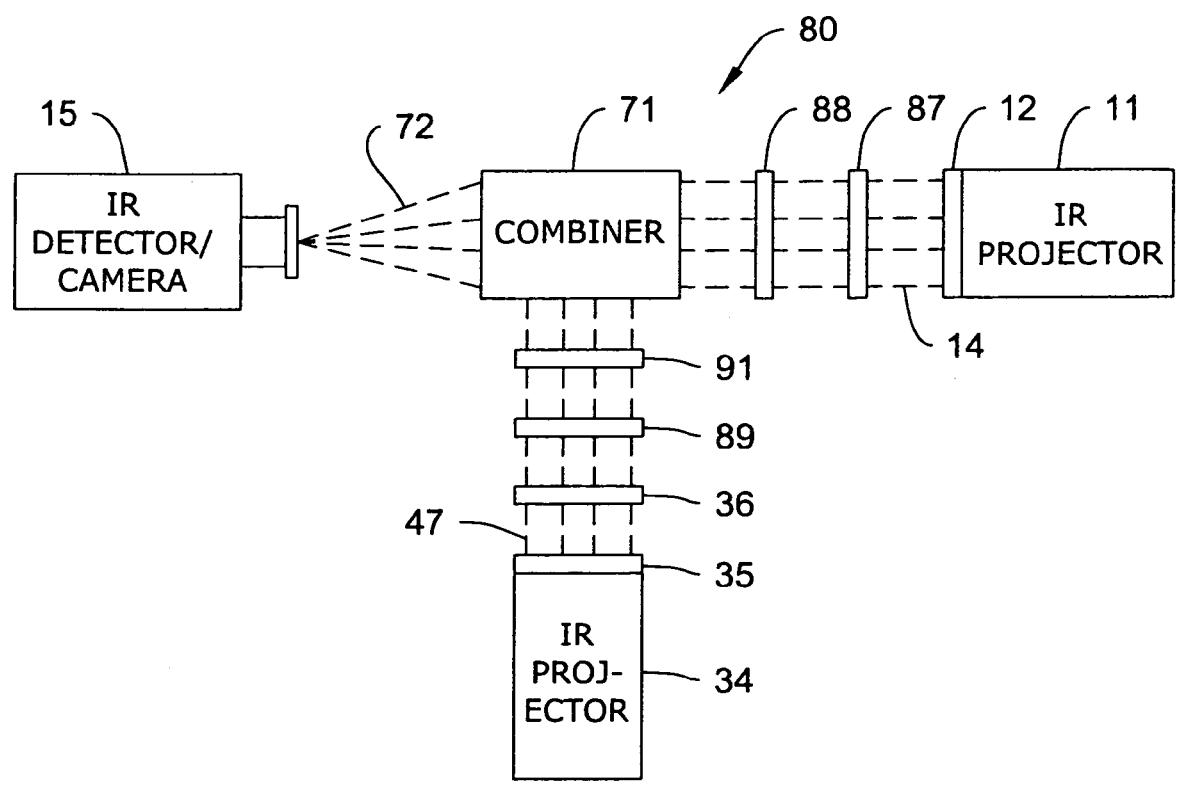
FIG. 10 reveals a multiple projector system where each projector has multiple filters.

FIG. 10 reveals a system 80 having a two-projector system, where each projector has several cells in front of it. Projector 11 with array 12 may emit a scene 14 that may have various spectra imposed on it by cells 87 and 88. Likewise, IR projector 34 with array 35 may emanate a scene 47 that propagates through cells 36, 89 and 91 which impose certain spectra on IR scene 47. The combination of various fluids in the cells may be selected to provide IR scenes with particular items exhibiting certain spectra, some of which may vary in percentage of composition over time. Scenes 14 and 47, after passage through and modification by cells 87, 88, 36, 89 and 91, respectively, may be put together into a resultant scene 72 by combiner 71. Combiner 71 may be of any technology and is not restricted to mirror types of devices. Camera 15 may detect scene 72 for various purposes.

Figure 11:
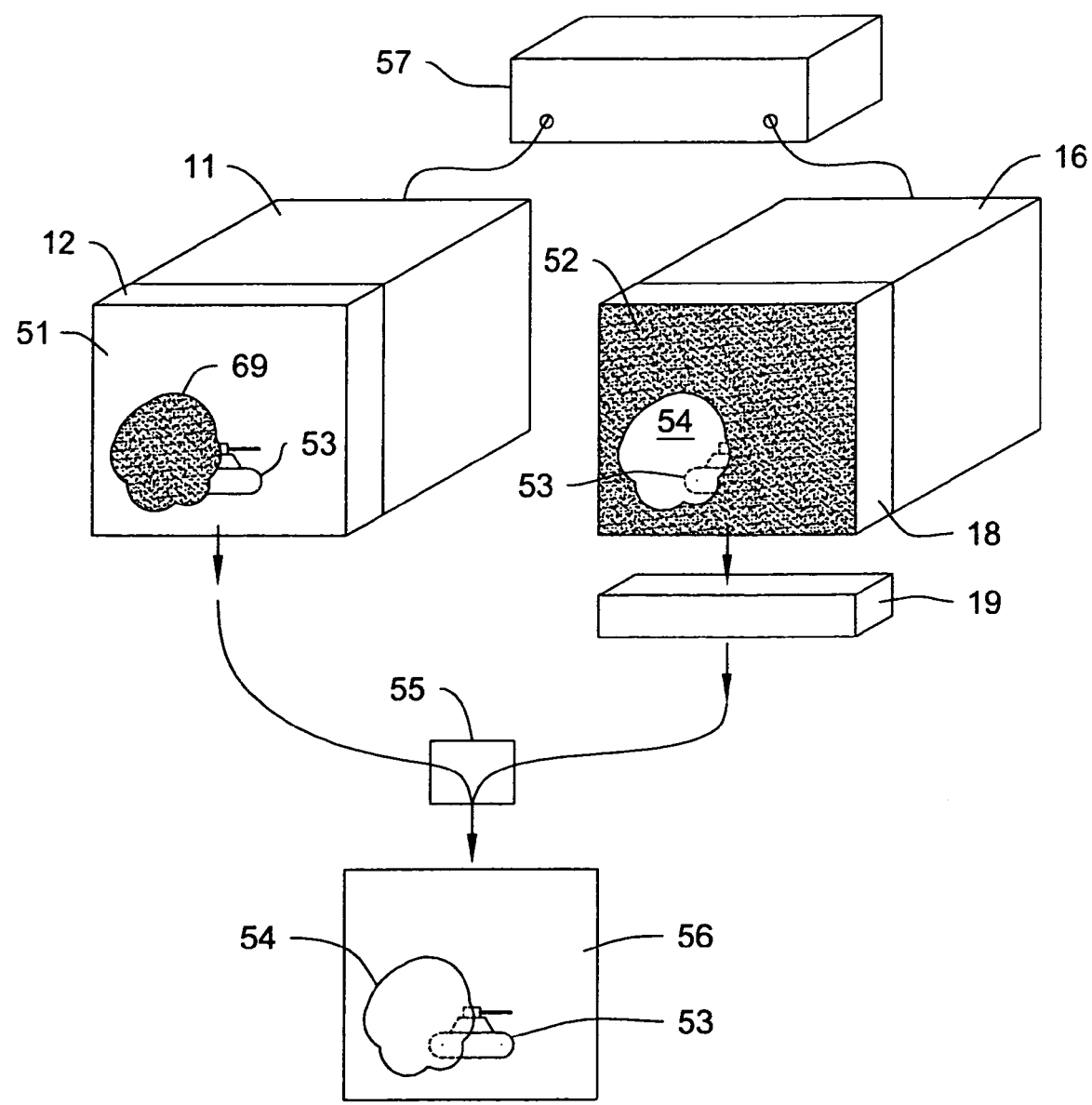
FIG. 11 is an illustrative example of combining a black body scene with another scene.

FIG. 11 is an illustrative scenario example of the combing of scenes. Array 12 may contain pixels like those, for example of a bolometer, except electric current is forced through some of the elements to make certain hot pixels in a pattern, resembling, for instance, a mobile military tank 53 which may be a black body in scene 51. The pixel content of array 12 or 18 may be, whatever one's design calls for, 100×100, 240×320 or 480×640 pixels, and so forth. Array 18 may be constructed like and operate similar to array 12. A cloud 54 may be presented in array 18 as scene 52 but that area of the cloud is a portion 69 of scene 51 that is missing. Portion 69 is not presented or lit up via the array pixels in scene 51. Its absence may be represented by the shading. The rest of scene 51 may be present, including a portion of tank 53. The shaded or darkened-out portion 69 may be the missing part of the scene and be an inactive portion of array 12 of pixels. Counterpart scene 52 may show cloud 54 having an outline of tank 53 which is in that portion of the scene. The resultant scene 56 may be the combination or sum of the actively presented portions of scenes 51 and 52. If the darkened areas were added together into a scene, the resultant scene may be completely darkened.

Projectors 11 and 16 may present the respective scenes via the arrays, which may be generated and coordinated by a computer 57. Cloud 54 may be a black body having a signature present with the signature of tank 53. Scene 52 may be projected through cell 19 containing a gas. Cell 19 can be regarded as an "optical signature modifier". Scene 51 and modified scene 52 may be combined at device 55. Various kinds of media may be utilized to convey and combine scenes 51 and 52. For instance, optical fiber may be used to transmit the modified infrared scene 52 and infrared scene 51 to device 55. Device 55 may be an optical coupler that combines these scenes into a scene 56. The spectral content of scene 51 may not be strictly black body in scene 56.

Figure 12A:
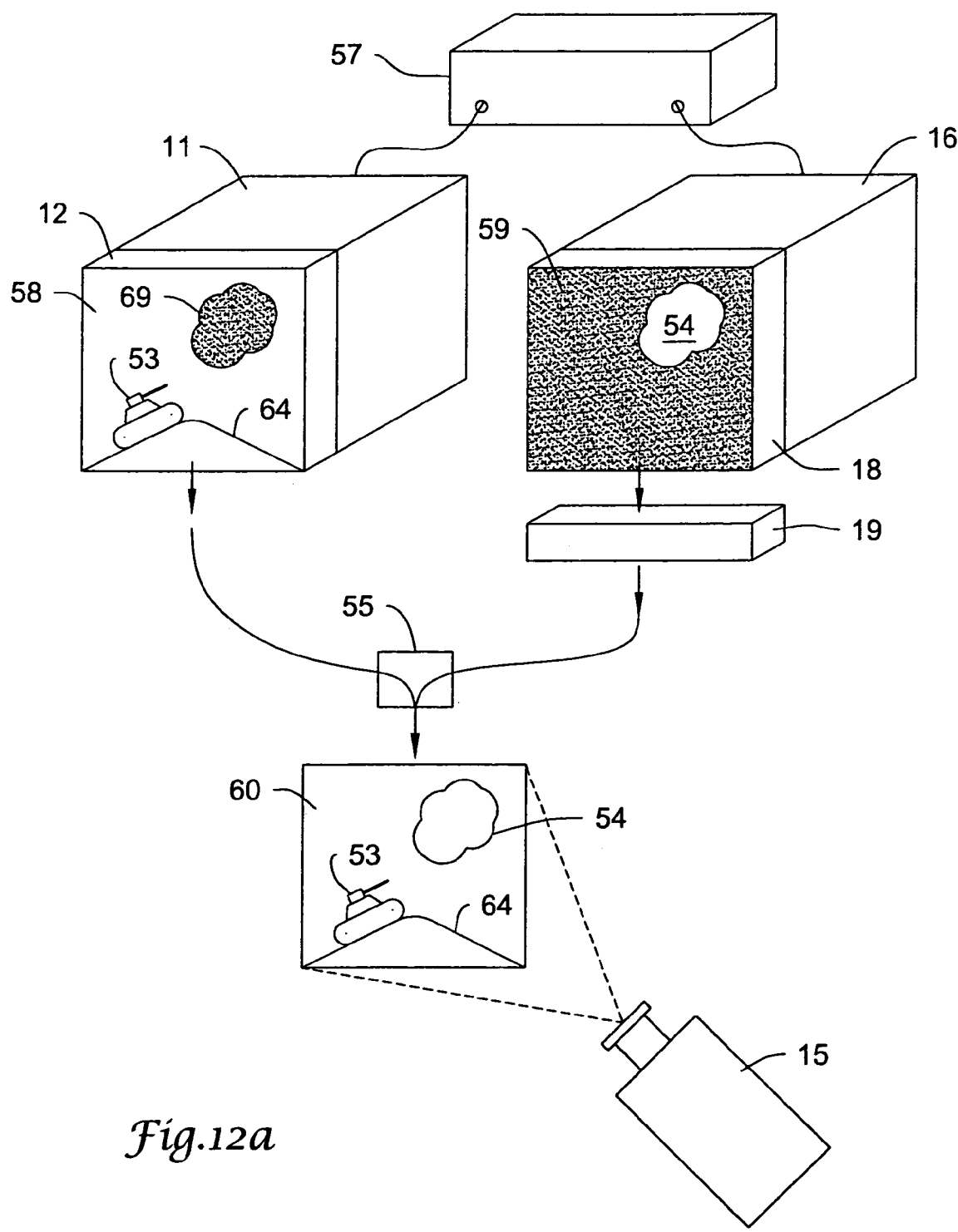
FIGS. 12a and 12b show a projector system revealing dynamic scenes.
Figure 12B:
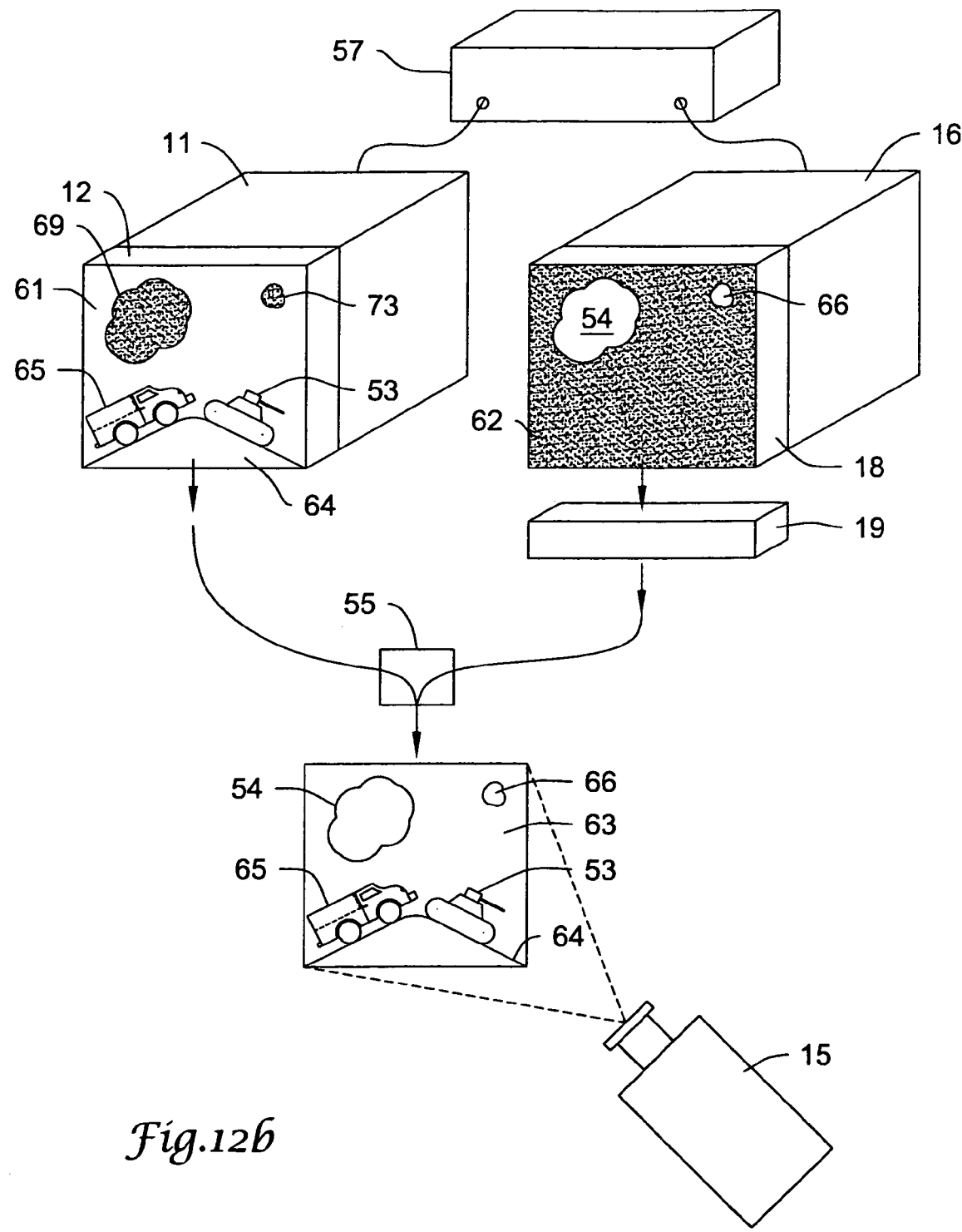

The same principle of active (light) and inactive (dark) portions of the scenes, shown above with FIG. 11, may apply to FIGS. 12a and 12b. The scenes may be dynamic with moving objects and clouds of gas. The present projection can generate a synthetic battle field that is dynamic as well. FIG. 12a may show tank 53 climbing a hill 64 in a scene 58 of array 12. That may be the active part of the scene 58. The inactive portion of scene 58 may be the shaded portion 69. No signal would come from the projector to that area of the scene. The active portion of scene 59 may be cloud 54. The remaining portion of array 18 is dark and inactive. If the two undarkened or lightened portions of scenes 58 and 59 are added together, then one may get the resultant scene 60. If the two darkened areas of arrays 12 and 18 are added together, then one may get a completely darkened scene or pixel array. Cloud 54 may be in scene 59 of array 18. Scene 59 may go through cell 19 and impose a spectra of the gas in cell 19 upon cloud 54 which appears in scene 60. Scenes 58 and 59 may be combined at device 55 into scene 60. Camera 15 may detect scene 60 with tank 53 on hill 64 and cloud 54 of agent gas.

FIG. 12b may show subsequent scenes 61 and 62 from the same projectors only moments later. These scenes in FIGS. 12a and 12b may show the dynamics of the projection system with an animation of moving objects. In FIG. 12b, tank 53 may be going downhill and a truck 65 may appear in scene 61 of array 12. In scene 62 of array 18, cloud 54 may move towards the left. A new cloud 66 may appear in scene 62. As scene 62 passes through device or cell 19 containing the gas, the spectra of the gas may be imposed on clouds 54 and 66. In the combined scene 63, there may be two vehicles and two clouds of the gas or agent. Infrared camera 15 may detect moving vehicles, shifting gas clouds and possibly other objects appearing and sometimes moving in dynamic infrared scene 63. Various battle scene scenarios may be provided in an infrared scene for significant evaluation of camera 15. Clouds 54 and 66 are not present in scene 61. The absence of the clouds may be indicated by missing portions of the scenes as indicated by darkened areas 69 and 73. Combining the lighter portions of scenes 61 and 18 may result in a complete scene 63. If the darkened parts of scenes 61 and 62 or inactivated portions of arrays 12 and 18, respectively, are combined or added together, then one may get a completely darkened screen or inactive array for a resultant scene (not shown).

Although the invention has been described with respect to at least one illustrative embodiment, many variations and modifications will become apparent to those skilled in the art upon reading the present specification. It is therefore the intention that the appended claims be interpreted as broadly as possible in view of the prior art to include all such variations and modifications.

What is claimed is:

1. A projection system comprising:
a first array projector;
a second array projector;
at least one absorption cell proximate to said second array projector; and
a radiation combiner proximate to said first and second array projectors.

2. The projection system of claim 1, wherein:
said at least one absorption cell contains a spectral simulant; and
said second array projector emanates a first scene through said at least one absorption cell resulting in a second scene having a spectra signature of the simulant.

3. The projection system of claim 2, wherein:
said first array projector emanates a third scene; and
said combiner combines the second and third scenes into a fourth scene.

4. The projection system of claim 3, wherein the fourth scene is available for sensing by an IR camera or the like which may be able to detect and identity the simulant in the fourth scene.

5. A scene projection system, comprising:
a first array for emitting a scene;
a second array for emitting the scene;
a cell exhibiting a signature of at least one agent or simulant, proximate to the second array; and
a combiner proximate to the first and second arrays and the cell.

6. The system of claim 5, wherein:
the scene is emitted from the second array through the cell and then combined with the scene emitted from the first array;
the scene as emitted by the first and second arrays has a signature; and
the signature of the scene from the second array is modified by the cell.

7. The system of claim 6, wherein the first and second arrays are black body emitters.

8. The system of claim 6, wherein the scene is dynamic in that it may reflect movement of at least one agent or simulant and other items in the scene.

9. A scene projection system comprising:
a plurality of projectors;
wherein:
each projector can project at least a portion of a scene;
some projectors of said plurality of projectors have at least one absorption cell situated proximate to the some projectors so that at least a portion of the scene is projected through the at least one absorption cell; and
at least one absorption cell adds spectra of at least one gas or simulant to the portion of the scene projected through the absorption cell; and
the at least one portion of the scene is combined with any other portion of the scene.

10. The scene projector system of claim 9, wherein at least one portion of a scene is projected in an infrared wavelength.

11. A scene projection system comprising:
a first projector array for projecting a first portion of a scene in a first waveband;
a second projector array for projecting a second portion of a scene in a second waveband; and
a beam combiner situated proximate to said first and second projector arrays; and
an absorption cell containing a gas, situated proximate to said second projector array; and
wherein:
said beam combiner substantially combines the first portion of the scene and the second portion of the scene into one scene; and
said beam combiner substantially transmits the first portion of the scene and substantially reflects the second portion of the scene to a common location in that the first and second portions are combined into one scene.

12. The projection system of claim 11, wherein absorption spectra of the gas are displayed in the one scene.

13. The projection system of claim 11, wherein at least one of the first and second wavebands may be different.

14. The projection system of claim 11, wherein the first and second portions of a scene may be whole portions.

15. The projection system of claim 11, wherein said first projector array comprises a plurality of pixels, and each pixel of the plurality of pixels is selectively heated to display the first portion of the scene in a first wavelength.

16. The projection system of claim 15, wherein said second projector array comprises a plurality of pixels, and each pixel of the plurality of pixels is selectively heated to display the second portion of the scene in a second wavelength.

17. A scene projection system comprising:
a first projector array for projecting a first portion of a scene in a first waveband;
a second projector array for projecting a second portion of a scene in a second waveband; and a beam combiner situated proximate to said first and second projector arrays; and wherein:

said beam combiner substantially combines the first portion of the scene and the second portion of the scene into one scene;

the first and second wavebands may be the same; and the first and second bandwidths may have the frequency spectra of a black body.

18. A projection system comprising:

means for projecting a first scene;

means for projecting a second scene;

means for imposing a spectra signature of an agent or simulant in the second scene;

means for combining the first scene and the second scene having the spectra signature, into a third scene;

means for projecting a fourth scene;

means for imposing a second spectra signature of a second agent or simulant in the fourth scene; and means for combining the third scene and the fourth scene having the second spectra signature, into a fifth scene.

19. The projection system of claim 18, further comprising:

means for projecting a sixth scene;

means for imposing a third spectra of a third agent or simulant in the sixth scene; and means for combining the fifth scene and the sixth scene having the third spectra signature, into a seventh scene.

20. A method of projecting scenes, comprising:

projecting a first scene;

projecting a second scene;

adding a simulation of an agent to the second scene;

combining the first scene with the second scene having the simulation of the agent, into a third scene;

projecting a fourth scene;

adding a simulation of a second agent to the fourth scene; and combining the third scene with the fourth scene having the simulation of the second agent, into a fifth scene.

* * * * *